US011077223B1

(12) United States Patent
Chapman et al.

(10) Patent No.: US 11,077,223 B1
(45) Date of Patent: *Aug. 3, 2021

(54) METHOD OF ORAL HEMOSTASIS USING A CONFORMABLE NON-DISRUPTIVE HEMOSTASIS MATERIAL

(71) Applicant: P.T. ROM and Associates LLC, Elkton, MD (US)

(72) Inventors: Frank M. Chapman, Elkton, MD (US); Randall F. Chapman, Elkton, MD (US)

(73) Assignee: P.T. ROM and Associates LLC, Elkton, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/830,551

(22) Filed: Mar. 26, 2020

Related U.S. Application Data

(63) Continuation-in-part of application No. 16/520,854, filed on Jul. 24, 2019, now abandoned, which is a continuation of application No. 15/695,044, filed on Sep. 5, 2017, now Pat. No. 10,413,631.

(51) Int. Cl.
    *A61L 15/24* (2006.01)
    *A61F 13/00* (2006.01)
    *A61L 15/42* (2006.01)

(52) U.S. Cl.
    CPC ........ *A61L 15/24* (2013.01); *A61F 13/00017* (2013.01); *A61F 13/00034* (2013.01); *A61L 15/42* (2013.01); *A61L 15/425* (2013.01); *A61F 2013/00272* (2013.01); *A61L 2400/04* (2013.01)

(58) Field of Classification Search
    CPC combination set(s) only.
    See application file for complete search history.

(56) References Cited

U.S. PATENT DOCUMENTS

| | | |
|---|---|---|
| 4,565,663 A | 1/1986 | Errede et al. |
| 6,436,135 B1 | 8/2002 | Goldfarb |
| 7,897,832 B2 | 3/2011 | McAdams et al. |
| 8,777,911 B2 | 7/2014 | Heagle et al. |
| 8,840,989 B2 | 9/2014 | Gvozdic |
| 10,086,105 B2 * | 10/2018 | Guo ................. A61F 13/00987 |
| 10,413,631 B1 * | 9/2019 | Chapman .......... A61F 13/00034 |
| 2007/0167971 A1 | 7/2007 | Huey et al. |
| 2012/0323155 A1 | 12/2012 | Buckman et al. |
| 2013/0035665 A1 | 2/2013 | Chu et al. |
| 2014/0248585 A1 | 9/2014 | Yang |

OTHER PUBLICATIONS

C.D. Campbell, et. al., The use of expanded microporous polytetrafluoroethylene for limb salvage: A preliminary report, 1976, Surgery, vol. 79, No. 5, p. 85-493, (Year: 1976).*
J. Morphol Science, vol. 29, No. 2, a Dimorphic Study of Maxillary First Molar Crown Dimensions of Urhobos in Abraka, South-Souther Nigeria, "Eboh".

* cited by examiner

*Primary Examiner* — Hasan S Ahmed
(74) *Attorney, Agent, or Firm* — Invention To Patent Services; Alex Hobson

(57) ABSTRACT

A method of promoting hemostasis in the mouth or oral cavity utilizes a non-absorbent, low surface energy and highly conformable non-disruptive hemostasis material. Traditional wound packing material is highly absorbent and has large open surfaces that allow clot forming materials, such as the platelet plug to adhere to the packing material and whereupon removal, the clot is disrupted. A non-disruptive highly conformable hemostasis material does not have large open pores and therefore does not adhere to forming clots. A non-disruptive hemostasis material may consist of expanded polytetrafluoroethylene that has a pore size of no more than about 10 microns. A non-disruptive hemostasis material may comprise a thin film of material over a portion of the outside surface that is non-absorbent and thin to allow for conforming into an oral cavity, such as from a tooth extraction. A thin film may cover porous material, such as a foam, that may be elastomeric.

20 Claims, 10 Drawing Sheets

Machine Direction

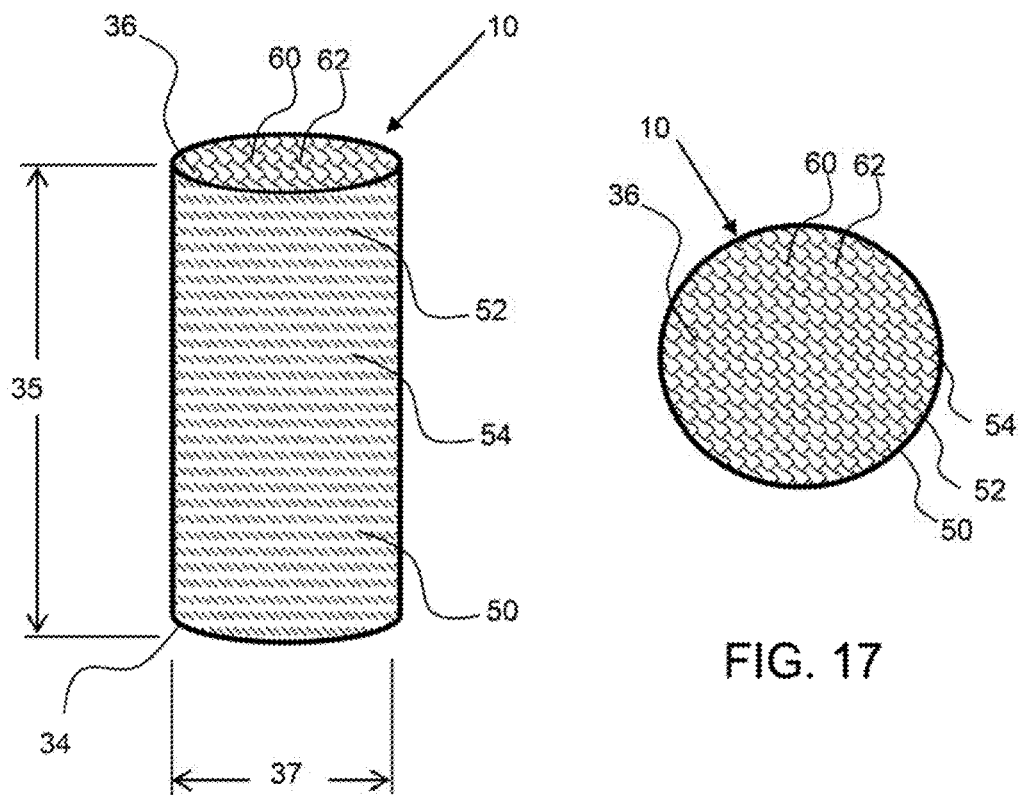
FIG. 16
FIG. 17
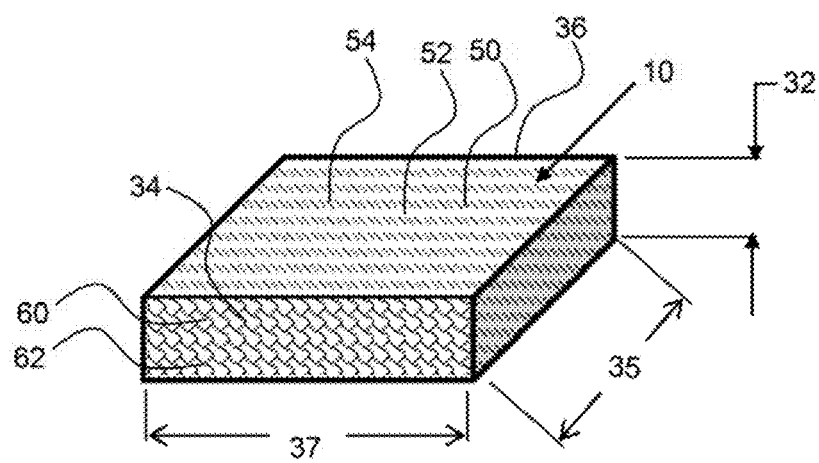
FIG. 18

METHOD OF ORAL HEMOSTASIS USING A CONFORMABLE NON-DISRUPTIVE HEMOSTASIS MATERIAL

CROSS REFERENCE TO RELATED APPLICATIONS

This application is a continuation in part of U.S. patent application Ser. No. 16/520,854, filed on Jul. 24, 2019 and currently pending, which is a continuation of U.S. patent application Ser. No. 15/695,044, filed on Sep. 5, 2017 and now issued as U.S. Pat. No. 10,413,631 on Sep. 17, 2019, the entirety of both applications are hereby incorporated by reference herein.

BACKGROUND OF THE INVENTION

Field of the Invention

The invention relates to a method of oral hemostasis or clot forming utilizing a hydrophobic highly conformable and non-disruptive hemostasis material

Background

The mouth has a lot of blood vessels and the additional moisture from salivary glands can make hemostasis and clot formation difficult. After a tooth extraction, oral surgery or other oral procedure, incisions or wounds in the mouth may bleed for a prolonged period of time, such as hours or days. Patients on blood thinners, or anticoagulants, such as heparin or warfarin (also called Coumadin), or antiplatelet drugs, such as aspirin, that prevent blood cells called platelets from forming a clot, may have more trouble clotting after a dental procedure. The application of a traditional absorbent or packing material to a treatment site in the mouth or oral cavity can be difficult, as adhesive bandages do not adhere within the wet environment of the mouth. Gauze or other packing materials that are inserted into an oral cavity or placed on an oral wound may absorb blood but do not effectively promote clot formation. They absorb the blood and can remove clot formation material, such as platelets, a platelet plug, fibrin strands, and blood cells, when replaced with new materials, thereby prolonging clot formation time.

When a tooth is extracted it can be difficult to place and maintain a dressing into the cavity formed by the extraction. Packing gauze or other wound dressing material can easily pop out of the cavity and overtime become saturated with blood and other oral liquids, thereby causing them to shrink down from a highly porous starting dimension. These dimensional changes from absorption of the oral liquids make maintaining these absorbent materials difficult.

SUMMARY OF THE INVENTION

The invention is directed to a method of promoting hemostasis in the mouth utilizing a non-absorbent, low surface energy and highly conformable non-disruptive hemostasis material. Traditional wound packing material is highly absorbent and has large open surfaces that allow clot forming material such as the platelet plug to adhere to the packing material. Removal of the packing material can remove the clot forming tissues, such as the platelets, the platelet plug, or clot and therefore disrupts the hemostasis process. It has been surprisingly discovered that a non-absorbent conformable material quickly and effectively produces clot formation and hemostasis of oral wounds.

A non-disruptive hemostasis material is non-absorbent, having a surface energy that is much lower than that of water, saliva or blood. Water has a surface tension of about 72.8 dynes/cm at 20° C., saliva has a surface tension of about 40 to 50 dynes/cm, and blood has a surface tension of about 48 to 52 dynes/cm. An exemplary non-disruptive hemostasis material has a low surface energy, such as less than 25 dynes/cm, less than about 20 dynes/cm such as about 18 dynes/cm or less. An exemplary non-disruptive hemostasis material is hydrophobic. An exemplary non-disruptive hemostasis material may comprise a fluoropolymer, consistent essentially of a fluoropolymer or consists of a fluoropolymer. An exemplary fluoropolymer is polytetrafluoroethylene, which has a surface energy of about 20 dynes/cm. This low surface energy of the non-disruptive hemostasis material prevents liquid in the mouth, such as saliva, and blood products from wetting and absorbing into the non-disruptive hemostasis material.

An exemplary non-absorbent non-disruptive hemostasis material may have a porous outside surface or a non-porous outside surface. An exemplary non-porous non-disruptive hemostasis material will prevent any liquid from entering into the bulk of the non-disruptive hemostasis material. An exemplary non-disruptive hemostasis material having a porous outside surface may have a small pore size, wherein blood cells and other clot formation blood products are not substantially absorbed into the non-disruptive hemostasis material. Red blood cells are typically about 6 to 8 microns (μm) in diameter and white blood cells are typically 12 to 15 μm in diameter. An exemplary non-disruptive hemostasis material may have an average, or mean flow pore size, as measured with a, permeability porosimeter, from Porous Materials Inc. Ithaca, N.Y., of no more than about 15 μm, no more than about 10 μm and preferably no more than 6 μm to prevent blood products from entering into the bulk of the non-disruptive hemostasis material and/or adhering thereto. A material with a small pore size and low surface energy will prevent oral liquids around a wound including saliva and blood from entering into the material. A high pressure would be required for these oral liquids to penetrate into the pores of a non-absorbent non-disruptive hemostasis material, as described herein.

A non-absorbent non-disruptive hemostasis material may have very little weight gain after application to a wound site. For example, an exemplary non-disruptive hemostasis material may be applied to an oral wound for an hour and upon removal may have less than a 20% weight gain, less than a 10% weight gain, or even than a 5% weight gain, whereby liquids do not absorb into the bulk of the non-disruptive hemostasis material. This may allow a user to re-use a non-disruptive hemostasis material as required until the wound has clotted. A traditional absorbent packing or wound dressing will typically have a weight gain of 50% or more and often 100% or more, as the oral liquids are absorbed and saturate the material. These absorbent packing materials are not re-usable.

A non-disruptive hemostasis material is highly conformable, wherein the material conforms under pressure to a non-uniform surface, such as an oral cavity. The material may be very soft and compliant, like a marshmallow, and have a Shore 00 hardness of 50 of less, about 40 or less, about 30 or less, about 20 or less, about 10 or less and any range between and including the softness values provided. The softer the material, the more compliant it will be to fill an oral cavity or to conform around and into a wound to prevent bleeding and promote clot formation. A marshmallow has a shore OO hardness of about 10 to 20, for example.

An exemplary non-disruptive hemostasis material comprises a conformable porous material that may have a high porosity, or percentage by volume of air. For example, an exemplary non-disruptive hemostasis material, or conformable porous material thereof, may have a porosity of 50% or more, about 70% or more, about 85% or more and any range between and including the porosity values provided. This high level of porosity enables a non-disruptive hemostasis material to conform to a surface or cavity to apply pressure to the wound. An exemplary non-disruptive hemostasis material may be compliant and non-elastic, wherein the material does not rebound to substantially an original shape after removal of a load that deforms the material. An exemplary non-disruptive hemostasis material may however have a negative Poisson's ratio, wherein the material will rebound back to substantially an original shape and volume after deformation by the application of tension. Poisson's ratio is the ratio of the proportional decrease in a lateral measurement to the proportional increase in length in a sample of material that is elastically stretched. For example, expanded polytetrafluoroethylene (ePTFE) has a negative Poisson's ratio and a rod of ePTFE after compressing the rod in the diameter direction, such as by pinching, will rebound to substantially an original diameter with the application of tension along the length of the rod. This unique property of ePTFE enables a user to remove the non-disruptive hemostasis material stretch it and then replace it over an oral wound and re-conform it to the wound. An exemplary non-disruptive hemostasis material may consist essentially of ePTFE, and the ePTFE may be in the shape of a rod having a negative Poisson's ratio. A rob shaped ePTFE material may be re-usable as it does not absorb or become saturated with water, saliva or blood.

An exemplary non-disruptive hemostasis material may be placed into the mouth, such as over a tooth extraction site and a patient may simply bite down to cause the non-disruptive hemostasis material to conform down into the extraction cavity and stop the bleeding and promote hemostasis. An example non-disruptive hemostasis material may be placed over a tooth extraction site with a portion extending over an adjacent tooth or adjacent teeth.

An exemplary non-disruptive hemostasis material may be or include an expanded fluoropolymer, such as expanded polytetrafluoroethylene (ePTFE), that comprises nodes interconnected by fibrils. Nodes are the intersection of two or more fibrils, and are a larger dense portion of the polymer from which fibrils extend from. Nodes may have an aspect ratio of length to width of about 1:1, about 2:1, about 4:1 or more and any range between and including the values provided. An exemplary ePTFE material may have a porosity of greater than 50%, such as more than 70%. An exemplary ePTFE may have an average pore size that is less than 10 μm to prevent blood products from entering into the pores of the ePTFE non-disruptive hemostasis material. An exemplary ePTFE non-disruptive hemostasis material has a surface energy of 18 to 20 dynes/cm and may have a porous or non-porous surface. A surface of an exemplary ePTFE non-disruptive hemostasis material may be non-porous having substantially no openings, and may comprise a film of low surface energy material, such as another fluoropolymer including, but not limited to, PTFE, fluorinated ethylene propylene (FEP) and the like. A surface of an exemplary ePTFE non-disruptive hemostasis material may comprise a thermoplastic fluoropolymer that has a low surface energy, such as less than 25 dynes/cm. The thermoplastic fluoropolymer may be at least partially embedded into the pores of the ePTFE material to adhere it thereto. A surface of an exemplary ePTFE non-disruptive hemostasis material may comprise a polymer imbibed into the surface, such as a low surface energy silicone or urethane and the like. The surface polymer is preferably soft and compliant to allow the non-disruptive hemostasis material to conform to the surface of the wound. Also, the thickness of the surface polymer layer may be kept thin, such as less than 2 mm, or less than 1 mm, to enable the non-disruptive hemostasis material to conform to the surface of the wound. An exemplary non-disruptive hemostasis material may comprise a foam material, such as a urethane or silicone foam and may comprise a cover material, such as a thin film of plastic. The ends of the exemplary non-disruptive hemostasis material may be open to allow the foam to be compresses and to allow air to escaped out of the end. The foam non-disruptive hemostasis material may then rebound, or return substantially to an original shape, upon removal from a compressed state, such as compressed over a wound or treatment site. An exemplary non-disruptive hemostasis material may be a urethane open celled foam having a thin plastic film over the surface, such as polyethylene or fluoropolymer, for example, and the film may be less than 50 um thick to allow for conforming to the oral wound or cavity.

An exemplary non-disruptive hemostasis material may be a sheet, rod or tube. A sheet form of the non-disruptive hemostasis material may have a thickness that enables biting down to conform the non-disruptive hemostasis material into an extraction cavity, for example, and may be at least about 5 mm thick, at least about 10 mm thick, at least about 20 mm thick, at least about 30 mm thick, at least about 40 mm thick and any range between and including the thickness values provided. An exemplary non-disruptive hemostasis material may be a rod having a width or diameter that is at least about 20 mm, at least about 30 mm, at least about 40 mm and any range between and including the diameter values provided.

An exemplary non-disruptive hemostasis material may comprise a porous inner material and an outside surface layer. The inner porous material may be a different material from the outside surface layer. For example, the inner porous material may be a foam, an expanded fluoropolymer such as expanded ePTFE, a fabric and the like. The inner porous material may be elastomeric or resilient, wherein it will return to an original shape after removal of a deforming force or load. For example, an inner porous material may be a foam that when compressed springs back upon removal of the compressive force. An inner porous material may be selected to absorb fluids, such as saliva and/or blood. A portion of the inner porous material may be exposed to enable saliva and blood to collect therein. For example, the outside surface layer may form a cylinder around the inner porous layer and the ends of the cylinder may be open to expose the inner porous material. An exemplary inner porous material is an open cell foam, such as a polyurethane foam. The inner porous material may be hydrophilic and the outside surface layer may be hydrophobic. In an exemplary embodiment, the outside surface layer is a cylinder of expanded PTFE and the inner porous material is an open cell foam.

Definitions

Hemostasis is the physiological process by which bleeding ceases. There are three steps in Hemostasis, vascular spasm, the formation of a platelet plug, and coagulation. In vascular spasm blood flows to the side of a ruptured vessel, the platelet plug blocks the flow of blood from the vessel and then clotting factors promote the formation of a fibrin clot.

Surface tension is the net intermolecular force on the surface molecules of a liquid. the tension of the surface film of a liquid caused by the attraction of the particles in the surface layer by the bulk of the liquid, which tends to minimize surface area. Surface energy is the relevant energy of these bonds and test to determine the surface energy of a solid may be performed using a Dyne Test kit having a plurality of liquids of different surface tension. The critical contact angle is measured or determined by placing drops of the various liquids on the surface of the solid. The solid will have a surface energy equivalent to the liquid that quickly wets the surface, such as within about two seconds. Accu Dyne test liquids are available from Diversified Enterprises, Claremont, N.H.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 16 shows a perspective view of a rod shaped non-disruptive hemostasis material comprising a porous inner material having an outside surface layer.

FIG. 17 shows an end view of a rod shaped non-disruptive hemostasis material comprising a porous inner material having an outside surface layer.

FIG. 18 shows a perspective view of a block of non-disruptive hemostasis material comprising a porous inner material having an outside surface layer.

Figure 1:
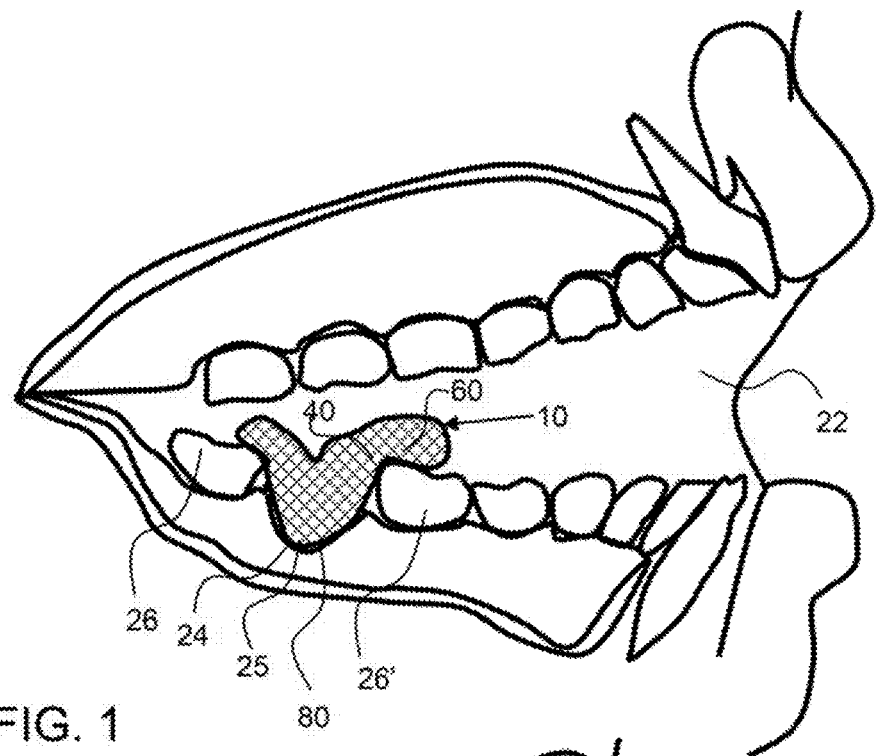
FIG. 1 shows a side view of an exemplary non-disruptive hemostasis material configured over an oral wound in an oral cavity to form a clot.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present Invention.

As shown in FIG. 1, an exemplary non-disruptive hemostasis material 10 is configured over an oral wound 24 in an oral wound cavity 25 to form a clot 80. The non-disruptive hemostasis material extends over the two adjacent teeth 26, 26' and down into the extraction site and conforms to the oral wound cavity. The non-disruptive hemostasis material comprises a conformable inner porous material 60 such as expanded polytetrafluoroethylene 80. As described herein, a non-disruptive hemostasis material may be used to promote hemostasis and clot formation of a wound in the mouth 22.

Figure 2:
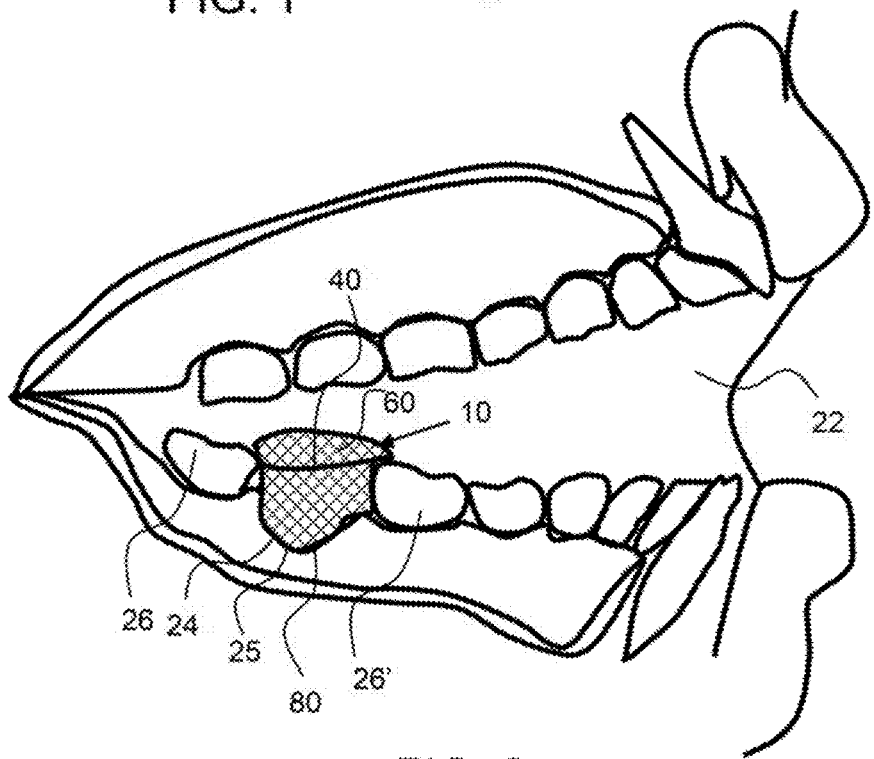
FIG. 2 shows a side view of an exemplary non-disruptive hemostasis material configured over an oral wound in an oral cavity to form a clot.

As shown in FIG. 2, an exemplary non-disruptive hemostasis material configured over an oral wound 24 in an oral wound cavity 25 to form a clot 80. The rod shaped non-disruptive hemostasis material has been forced down into the oral wound cavity by simply biting down. The soft non-disruptive hemostasis material conforms into the oral cavity to provide pressure to slow and prevent bleeding and to promote clot formation.

Figure 3:
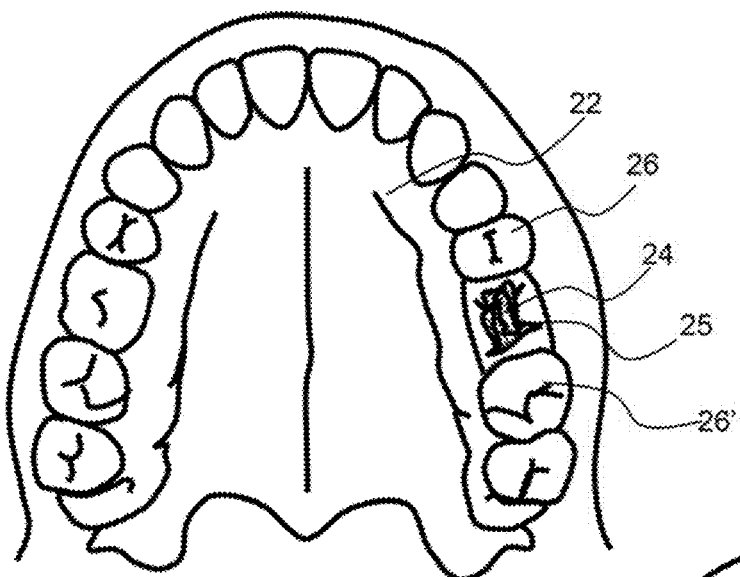
FIG. 3 shows a top-down view of a mouth having an oral wound in an oral cavity from a tooth extraction.
Figure 4:
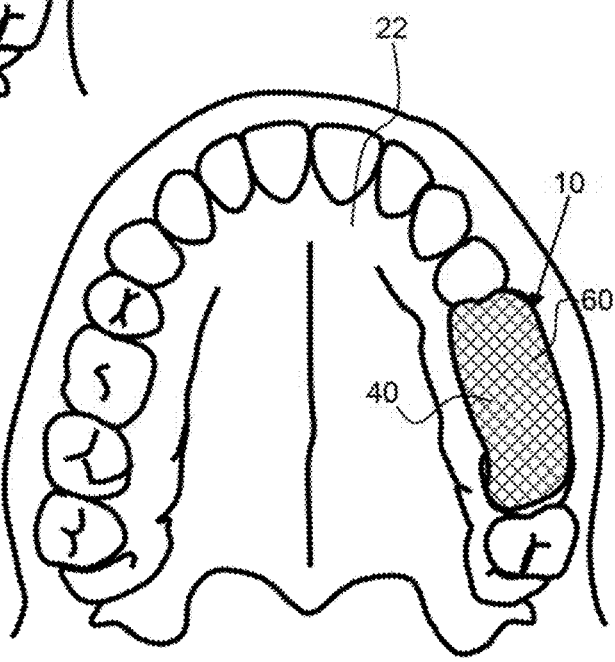
FIG. 4 shows a top-down view of an exemplary non-disruptive hemostasis material configured in the oral cavity shown in FIG. 3, and extending over adjacent teeth to the extraction site.
Figure 5:
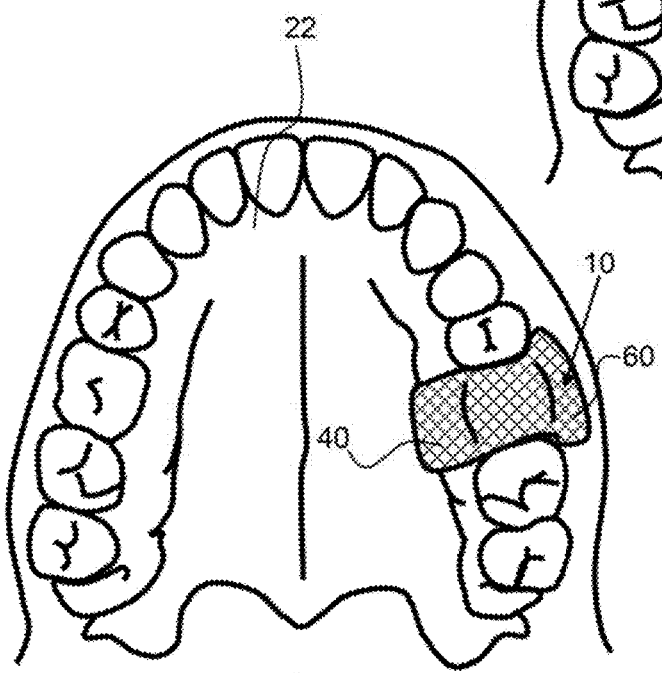
FIG. 5 shows a top-down view of an exemplary non-disruptive hemostasis material configured in the oral cavity shown in FIG. 3, and extending between adjacent teeth to the extraction site.

Referring now to FIGS. 3 to 5, a mouth 22 has an oral wound in an oral wound cavity 25 from a tooth extraction. As shown in FIG. 4, the non-disruptive hemostasis material 10 is configured in the oral wound cavity, as shown in FIG. 3 and is extending over the adjacent teeth 26, 26' and into the oral wound cavity. As shown in FIG. 5, an exemplary non-disruptive hemostasis material 10 is configured in the oral wound cavity, as shown in FIG. 3, and is extending between the adjacent teeth 26, 26' and into the oral wound cavity. In both cases, a patient may insert the non-disruptive hemostasis material over the wound and simply bite down to force the soft and compliant material to conform to the wound cavity.

Figure 6:
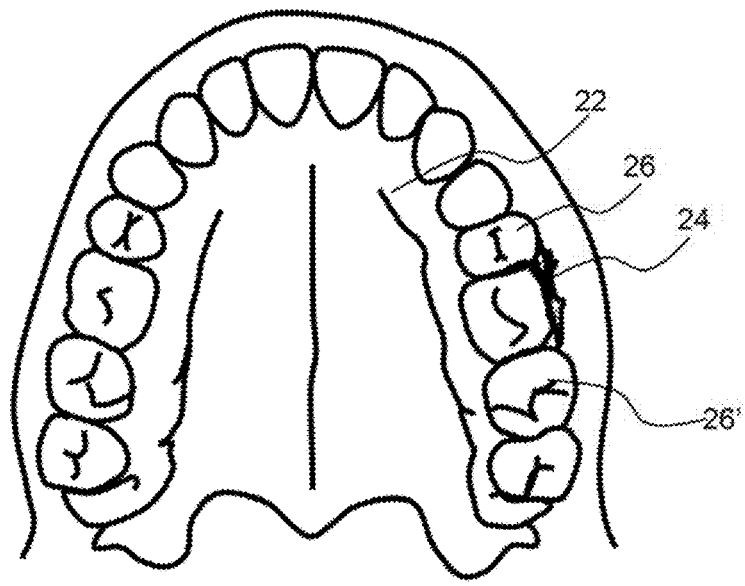
FIG. 6 shows a top-down view of a mouth having an oral wound between the teeth and the gum, or inside gum wall.
Figure 7:
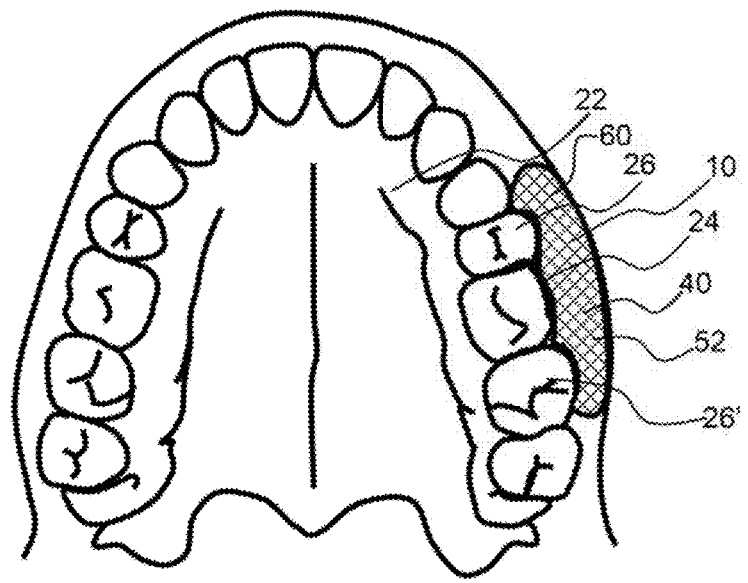
FIG. 7 show a top-down view of an exemplary non-disruptive hemostasis material configured in the oral wound shown in FIG. 6 and between the wound and the inside gum wall.

Referring now to FIGS. 6 and 7, a mouth 22 has an oral wound 24 between the teeth and the gum, or inside gum wall. As shown in FIG. 7, a non-disruptive hemostasis material 10 is configured over the oral wound 24 and between the wound and the inside gum wall, wherein pressure is applied by the gum wall to conform the non-disruptive hemostasis material to the wound. The non-disruptive hemostasis material 10 comprises an outside surface layer 52.

Figure 8:
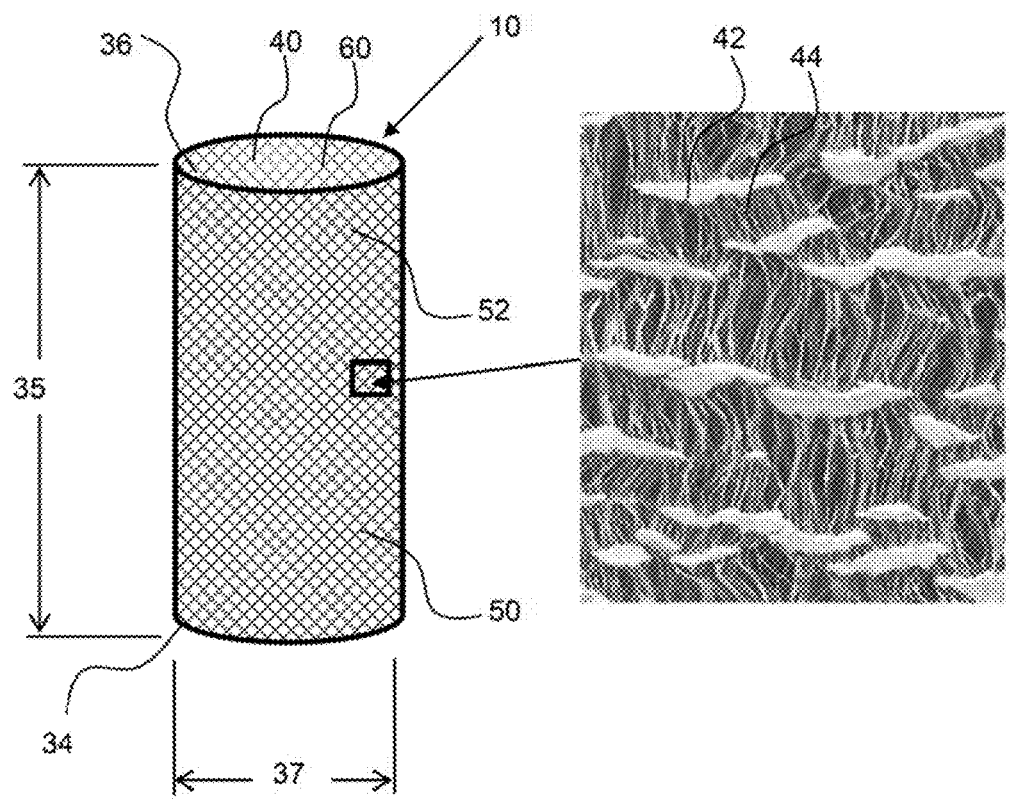
FIG. 8 shows a perspective view of an exemplary non-disruptive hemostasis material in the form of a rod having a length, a diameter and microstructure.

As shown in FIG. 8, an exemplary non-disruptive hemostasis material 10 is in the form of a rod having a length 35, a diameter 37 and microstructure as indicated by the enlarged SEM. The exemplary non-disruptive hemostasis material is expanded fluoropolymer 40, such as expanded polytetrafluoroethylene. The outside surface 50 may be porous as shown or comprise an outside surface layer 52 that forms a film layer on the outside surface. The expanded fluoropolymer 40 may be expanded polytetrafluoroethylene comprising nodes 42 interconnected by fibrils 44. As described herein, an outside surface layer may be substantially non-permeable, having substantially no pores or openings. An outside surface layer may produce a non-disruptive hemostasis material that is substantially non-permeable through the outside surface having a Gurley value as measure by an automatic 4340 Gurley densometer, from Gurley Precision Instruments Inc. of more than about 200 seconds or more than about 500 seconds.

Figure 9:
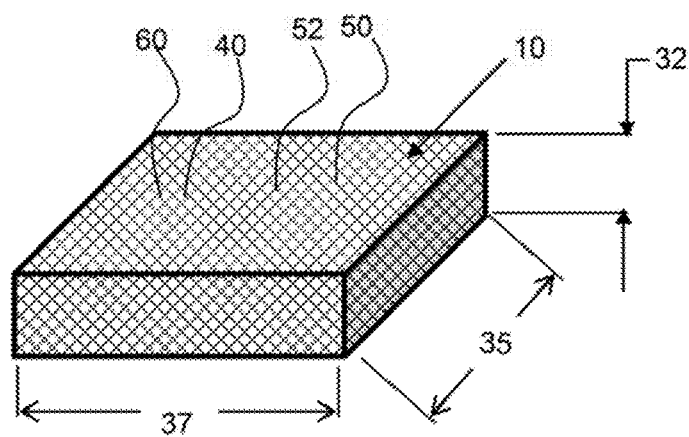
FIG. 9 shows a perspective view of an exemplary non-disruptive hemostasis material in the form of a sheet having a length, width and thickness.

As shown in FIG. 9, an exemplary non-disruptive hemostasis material 10 is in the form of a sheet or block having a length 25, width 37 and thickness 32.

Figure 10:
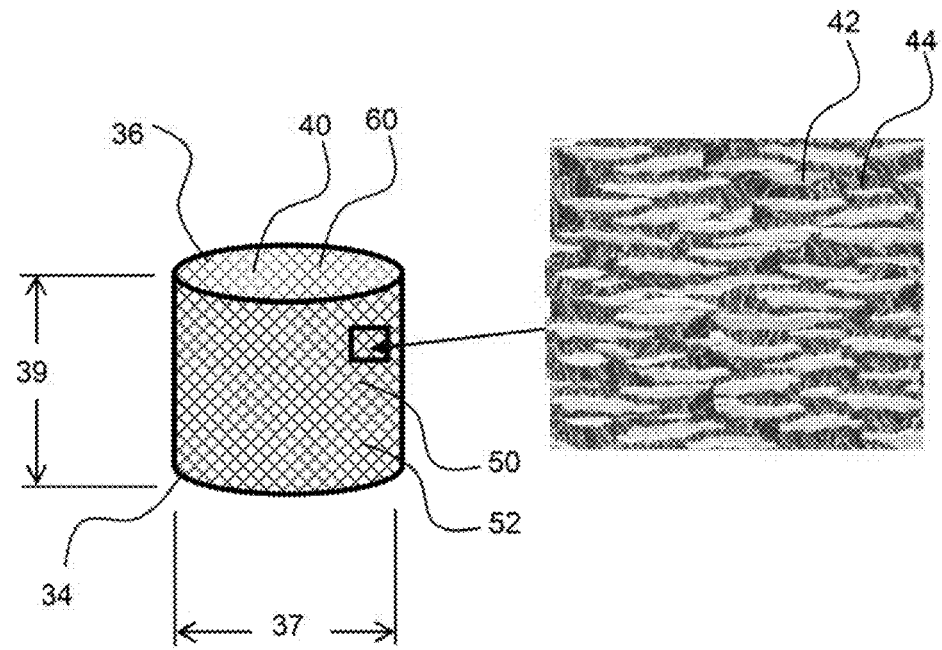
FIG. 10 shows a perspective view of the exemplary non-disruptive hemostasis material shown in FIG. 8 now compressed in the length direction and the associated compressed microstructure with the nodes collapsed more proximal to each other.

As shown in FIG. 10, the exemplary non-disruptive hemostasis material 10 shown in FIG. 8 is compressed in the length direction to a compressed length 39 and the compressed microstructure is shown with the nodes 42 collapsed to produce a denser outside surface that has smaller pores or opening. The nodes are closer to each other to produce a more dense surface that may promote clot formation and hemostasis.

Figure 11:
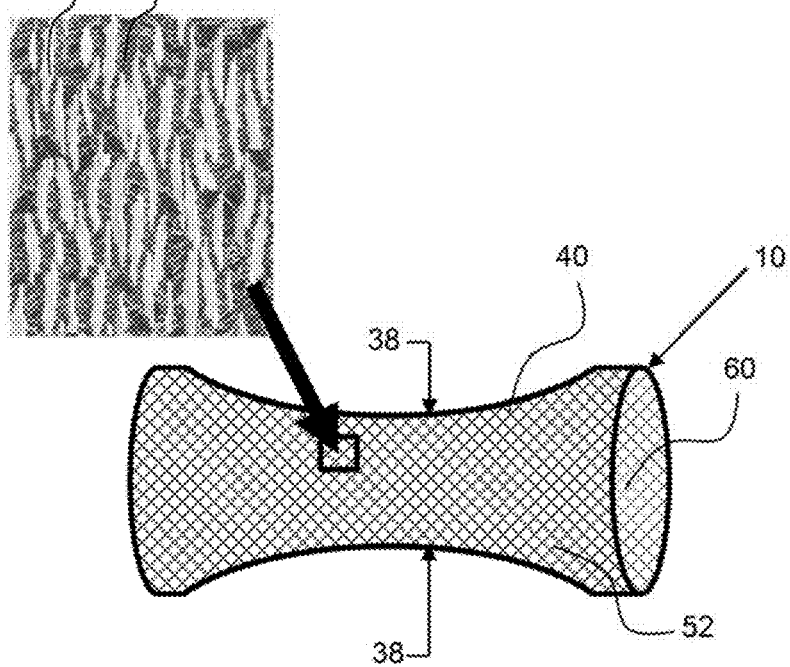
FIG. 11 shows exemplary a side perspective view of the non-disruptive hemostasis material shown in FIG. 8 now compress in the diameter dimension.

As shown in FIG. 11, the exemplary non-disruptive hemostasis material 10 shown in FIG. 8 now compress in the diameter dimension and has a compressed width 38 or diameter. Again, the nodes 42 are compressed towards each other, providing a more dense surface.

Figure 12:
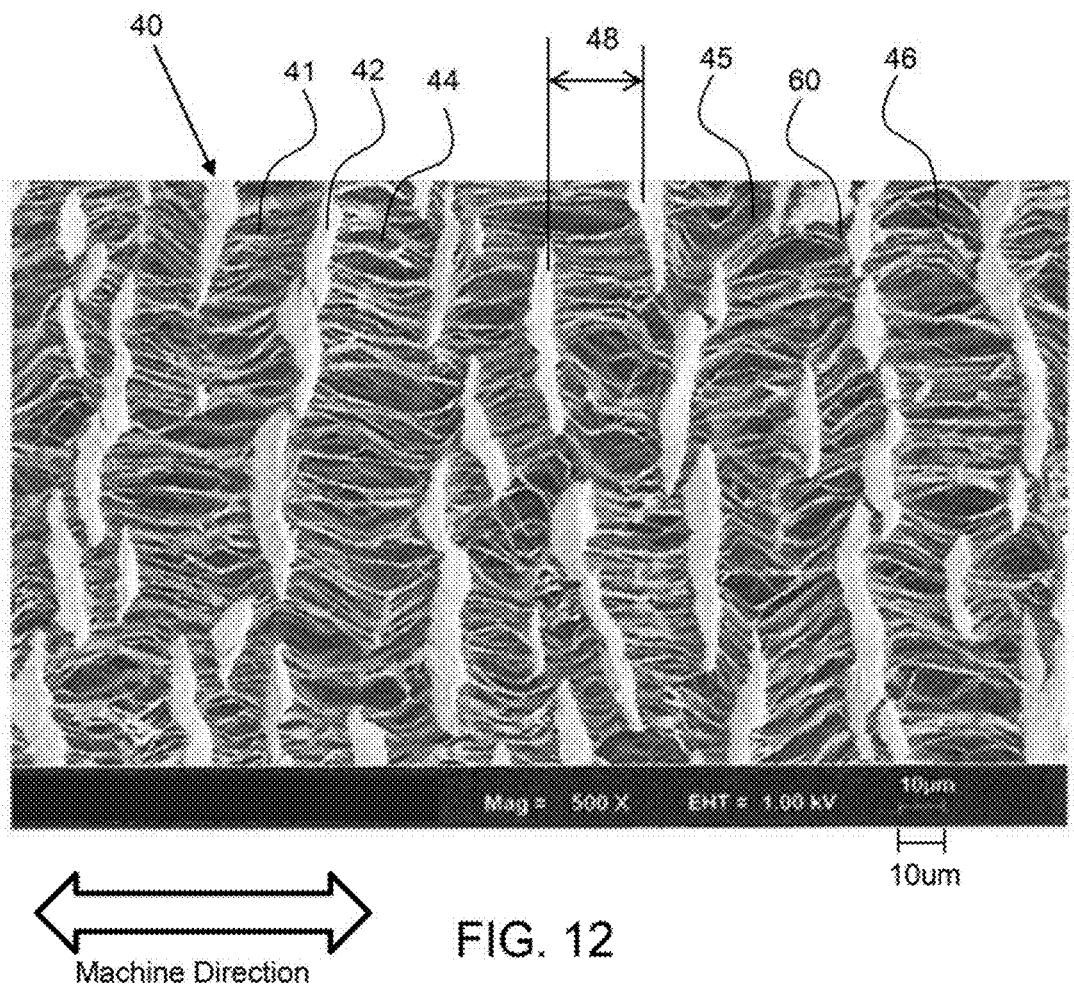
FIG. 12 shows a scanning electron micrograph (SEM), of the microstructure of expanded polytetrafluoroethylene having nodes interconnect by fibrils.

As shown in FIG. 12, the microstructure of expanded polytetrafluoroethylene 41, ePTFE, has nodes 42 interconnect by fibrils 44. The internodal distance 48, the distance between adjacent nodes, is about 30 microns and the pore size is less than 10 microns, as there are a plurality of fibrils extending between and interconnecting each of the nodes. The ePTFE is porous having a plurality of pores 46 creating porosity 45 in the material. The nodes have a length that runs perpendicular to the machine direction or length of the rod or sheet material. This microstructure may be on the surface or throughout the bulk of the ePTFE material.

Figure 13:
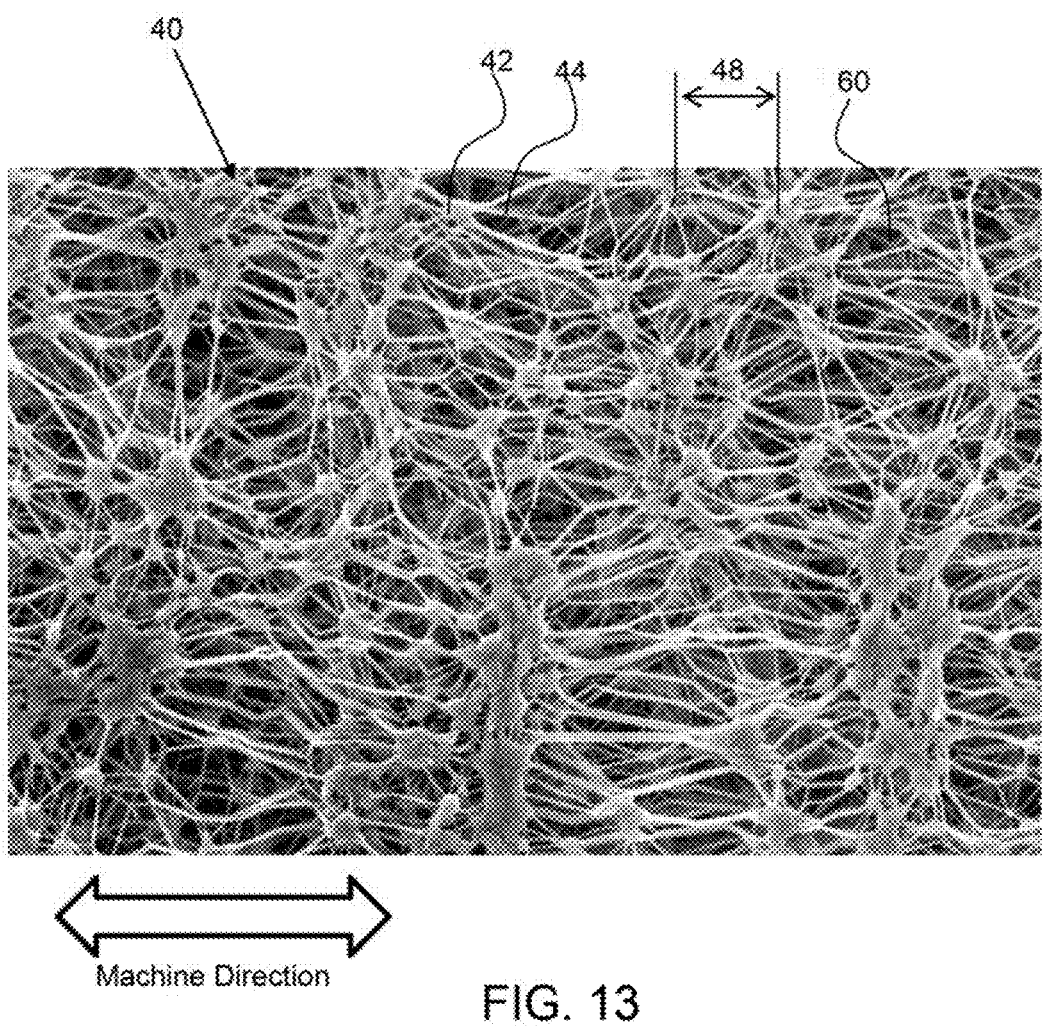
FIGS. 13 to 15 show scanning electron micrographs of exemplary ePTFE material.
Figure 14:
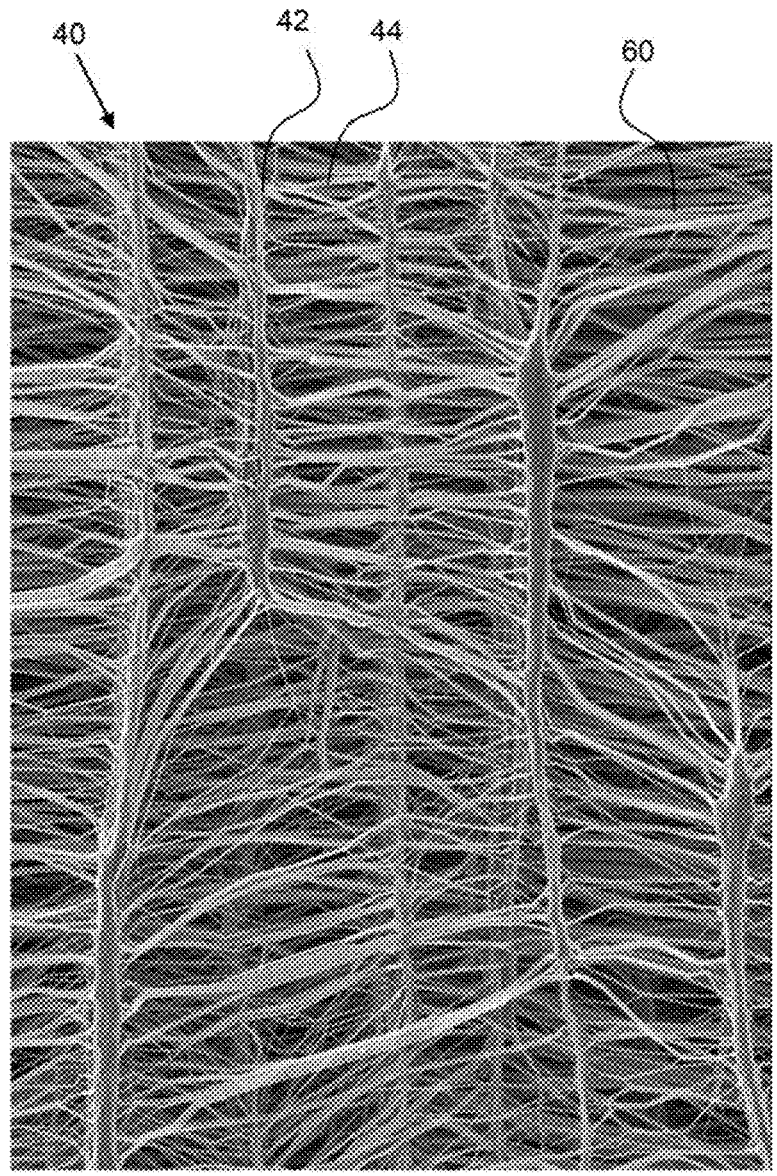
Figure 15:
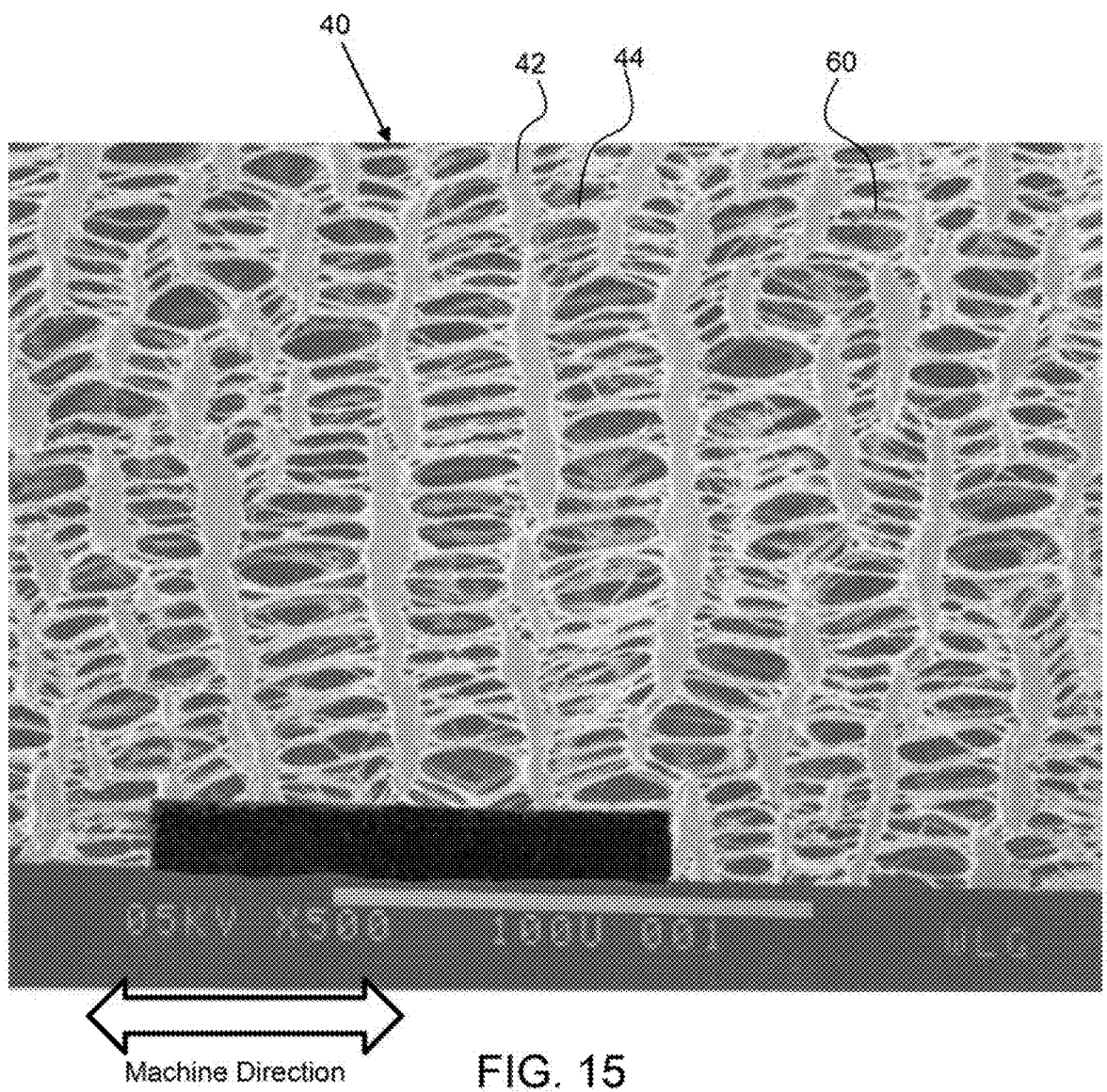

As shown in FIGS. 13 to 15, exemplary expanded polytetrafluoroethylene 40, ePTFE, material can be made in a variety of microstructures. As shown in FIG. 13, the nodes are smaller and the internodal distance 48 may be about 3 microns. As shown in FIG. 14, the nodes 42 are elongated, having a length that is much greater than the width of the node. As shown in FIG. 15, the fibrils 44 are more course are larger in the width direction than the fibrils of the ePTFE material shown in FIG. 12.

As shown in FIGS. 16 and 17, a rod shaped non-disruptive hemostasis material 10 comprises a porous inner material 60, such as a foam 62, having an outside surface layer 52 on a portion of the outside surface 50. The outside surface layer may be a thin film 54, that is non-porous and does not allow liquid to pass through to the inner porous material 60. As detailed herein, the outside surface layer may be expanded PTFE and may be a cylinder of expanded PTFE configured around the inner porous material. The surface layer covers the length 35 portion of the rod, but does not extend over the ends, 34 36. As described herein, the outside surface layer may be thin, such as less than 75 microns, or less than 50 microns, or less than 25 microns for conforming to the contours of a wound or oral cavity. Note that a foam material may be open cell or closed cell. A closed cell foam will not absorb moisture and may have less compression than an open cell foam that allows air and liquids to enter into the pores of the foam, and allows air within the cells to escape as the open cell foam is compressed. An outside surface layer may extend over the entire outer surface of the non-disruptive hemostasis material and may be non-porous, such as a film of polymer.

As shown in FIG. 18, a block of non-disruptive hemostasis material 10 comprises a porous inner material 60, such as a foam 62, having an outside surface layer 52 on a portion of the outside surface 50. The outside surface layer extends around the length 35 but does not cover the ends 34, 36. Again, an outside surface layer may extend over the entire outer surface of the non-disruptive hemostasis material and may be non-porous, such as a film of polymer It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A method of promoting clot formation in an oral cavity comprising the steps of:
    a) providing a conformable hydrophobic non-disruptive hemostasis material comprising:
        i) a thickness of at least 10 mm;
        ii) a shore 00 hardness of no more than 50; and
        iii) a low surface tension of no more than 25 dynes/cm; and
        iv) an outside surface layer consisting of expanded polytetrafluoroethylene;
            wherein the outside surface layer has an average pore size of no more than 10 microns to prevent blood products from entering into the outside surface layer and adhering thereto;
        v) a conformable porous material;

wherein the outside surface layer extends around the conformable porous material;

b) placing the non-disruptive hemostasis material over an oral wound with the outside surface layer against the oral wound;

c) applying pressure to the non-disruptive hemostasis material to force the non-disruptive hemostasis material to conform to the oral wound;

d) allowing a clot to form in the oral wound; and e) removing the non-disruptive hemostasis material without removing the clot.

2. The method of promoting clot formation in an oral cavity of claim 1, wherein the step of applying pressure comprises biting down on the non-disruptive hemostasis material.

3. The method of promoting clot formation in an oral cavity of claim 1, wherein the oral wound is an oral cavity from a tooth extraction.

4. The method of promoting clot formation in an oral cavity of claim 3, wherein the step of applying pressure comprises biting down on the non-disruptive hemostasis material wherein pressure is applied by biting down on the non-disruptive hemostasis material.

5. The method of promoting clot formation in an oral cavity of claim 1, wherein the outside surface layer is expanded polytetrafluoroethylene having nodes interconnected by fibrils; and wherein the expanded polytetrafluoroethylene material has an average pore size of no more than 10 microns to prevent blood products from entering into the expanded polytetrafluoroethylene and adhering thereto.

6. The method of promoting clot formation in an oral cavity of claim 5, wherein the expanded polytetrafluoroethylene has an average pore size of no more than 6 microns.

7. The method of promoting clot formation of claim 5, wherein the expanded polytetrafluoroethylene has a low surface tension of no more than 20 dynes/cm.

8. The method of promoting clot formation of claim 1, wherein the outside surface layer is substantially non-permeable having a Gurley value of 200 seconds or more.

9. The method of promoting clot formation in an oral cavity of claim 1, wherein the non-disruptive hemostasis material has a thickness of more than 20 mm.

10. The method of promoting clot formation in an oral cavity of claim 1, wherein the non-disruptive hemostasis material is rod shaped wherein the thickness is a diameter of the rod shaped non-disruptive hemostasis material.

11. The method of promoting clot formation in an oral cavity of claim 1, wherein the non-disruptive hemostasis material has a negative Poisson's ratio.

12. The method of promoting clot formation of claim 1, wherein the outside surface layer is a tube that extends around the conformable porous material.

13. The method of promoting clot formation of claim 12, wherein the conformable porous material is a foam.

14. The method of promoting clot formation of claim 13, wherein the foam is an open cell foam.

15. The method of promoting clot formation of claim 14, wherein the foam is a hydrophilic foam and wherein the foam is configured to absorb bodily fluids.

16. The method of promoting clot formation of claim 1, wherein the outside surface layer extends completely around a conformable porous material.

17. The method of promoting clot formation of claim 1, wherein the outside surface layer comprises a non-permeable thin film having a thickness of no more than 2 mm.

18. The method of promoting clot formation of claim 1, wherein the outside surface layer is a non-permeable thin film of fluoropolymer having a thickness of no more than 2 mm.

19. The method of promoting clot formation of claim 18, wherein the non-permeable thin film has a Gurley value of 200 seconds or more.

20. A conformable hydrophobic non-disruptive hemostasis material comprising:

i) a thickness of at least 10 mm;

ii) a shore OO hardness of no more than 50; and iii) a low surface tension of no more than 25 dynes/cm; and iv) a tube forming an outside surface layer consisting of expanded polytetrafluoroethylene having nodes interconnected by fibrils;

wherein the outside surface layer has an average pore size of no more than 10 microns to prevent blood products from entering into the outside surface layer and adhering thereto:

wherein the expanded polytetrafluoroethylene is hydrophobic:

v) a conformable porous material;

wherein the outside surface layer extends around the conformable porous material.

* * * * *